United States Patent
Russell et al.

(10) Patent No.: US 10,908,141 B2
(45) Date of Patent: Feb. 2, 2021

(54) METHODS AND KITS FOR DETECTING NON-LUMINESCENT OR WEAKLY LUMINESCENT METALS

(71) Applicant: New York University, New York, NY (US)

(72) Inventors: Stewart Russell, New York, NY (US); Edward A. Fisher, Scarsdale, NY (US); Youssef Zaim Wadghiri, New York, NY (US); Ryan Casey, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/821,647

(22) Filed: Nov. 22, 2017

(65) Prior Publication Data

US 2019/0271677 A1   Sep. 5, 2019

Related U.S. Application Data

(63) Continuation of application No. 14/384,020, filed as application No. PCT/US2013/029272 on Mar. 6, 2013, now abandoned.

(60) Provisional application No. 61/608,756, filed on Mar. 9, 2012.

(51) Int. Cl.
| | | |
|---|---|---|
| *G01N 33/20* | (2019.01) | |
| *G01N 21/64* | (2006.01) | |
| *G01N 21/77* | (2006.01) | |
| *G01N 21/55* | (2014.01) | |
| *G01N 24/08* | (2006.01) | |
| *A61K 49/00* | (2006.01) | |
| *A61K 49/10* | (2006.01) | |

(52) U.S. Cl.
CPC ......... *G01N 33/20* (2013.01); *A61K 49/0021* (2013.01); *A61K 49/105* (2013.01); *G01N 21/55* (2013.01); *G01N 21/6428* (2013.01); *G01N 21/77* (2013.01); *G01N 24/08* (2013.01); *G01N 2021/7786* (2013.01)

(58) Field of Classification Search
CPC ............ A61K 49/0013; A61K 49/0021; A61K 49/105; G01N 21/55; G01N 21/64; G01N 21/6428; G01N 24/08; G01N 33/20; G01N 2021/7786; Y10T 436/24
USPC ....... 436/73, 74, 81, 82, 164, 166, 172, 173; 422/82.05, 82.08; 250/200, 459.1; 324/307; 356/445
See application file for complete search history.

(56) References Cited

U.S. PATENT DOCUMENTS

| | | | | |
|---|---|---|---|---|
| 8,993,246 B2 * | 3/2015 | Soukka | ................ | C12Q 1/6818 435/7.1 |
| 9,732,378 B2 * | 8/2017 | Mustaev | ............... | C07D 215/38 |
| 2005/0064485 A1 * | 3/2005 | Vogel | ................. | G01N 21/6428 435/6.11 |
| 2006/0099148 A1 * | 5/2006 | Fisher | ................ | A61K 49/1806 424/9.34 |
| 2008/0194044 A1 * | 8/2008 | Faris | ..................... | C07C 229/76 436/537 |
| 2011/0189781 A1 * | 8/2011 | Klauth | .................... | C07F 5/003 436/94 |
| 2012/0107624 A1 * | 5/2012 | Klauth | ................... | C09K 11/02 428/446 |

OTHER PUBLICATIONS

Selvin et al. Journal of American Chemical Society, vol. 116, 1994, pp. 6029-6030.*

* cited by examiner

*Primary Examiner* — Maureen Wallenhorst
(74) *Attorney, Agent, or Firm* — Maxwell J. Petersen; FisherBroyles, LLP (57) ABSTRACT

The invention provides methods and kits for detecting the presence of, the amount of, or the concentration of a substantially non-emitting metal in a sample by a) providing a sensitizer to a chelator of the substantially non-emitting metal thereby creating a sensitized-metal complex; b) adding an unsensitized chelate, and c) detecting a signal from the unsensitized chelate. The substantially non-emitting metal may be gadoliniumn and may exist in complex with a chelator. The unsensitized chelate may be terbium (Tb) or europium (Eu) and the detecting a signal may be performed by fluorescence.

20 Claims, 6 Drawing Sheets

METHODS AND KITS FOR DETECTING NON-LUMINESCENT OR WEAKLY LUMINESCENT METALS

FIELD OF THE INVENTION

The present invention relates to methods and compositions for detecting non-luminescent or weakly luminescent metals.

BACKGROUND OF THE INVENTION

There are currently eight approved Gadolinium based MRI contrast agents (GBCA). The FDA indicates that three should not be used in patients with impaired kidney function. (Penfield, *Pediatric Nephrology*, 2008, 23(12): 2121-2129; Nacif, et al., *Journal of Cardiovascular Magnetic Resonance*, 2012, 14). Plasma clearance of GBCA may not be rapid enough in some patients to prevent buildup of free gadolinium in tissue. A number of academic and industry research labs are poised to introduce novel GBCA, and cite superior image enhancing capabilities and safer pharmacokinetic profiles in preliminary data, but the high cost and poor sensitivity of current methods of quantitative GBCA detection in plasma in the small-animal model makes it difficult for these labs to complete the necessary translational experiments. Novel agents will likely be required to be validated by animal kinetics studies. At the same time, the increased scrutiny continues to stimulate development of alternative GBCA that can avoid current health concerns. Because only 1 or 2 data points can be generated from a single mouse for plasma samples of 100 µL or larger, inter-animal variability can require researchers to collect on the order of 60 to 100 data points to accurately determine the plasma half-life of a GBCA. To evaluate a library of GBCA, the time and cost associated with quantification of Gd for kinetics studies will be prohibitive. (Bourasset, et al., *Magnetic Resonance Materials in Physics Biology and Medicine*, 2001, 12(2-3): 82-87; Telgmann, et al., *Journal of Chromatography*, 2012, 1240: 147-155). It is clear that an improved method of quantifying GBCA in plasma has the potential to usher in a new era of translational research.

Successful laboratories in this effort will likely be those with the capability for rapid and accurate evaluation of animal plasma kinetics. But the small animal model, which is important for rapid throughput evaluation of novel pharmaceuticals, is not up to the task for a simple reason: gadolinium is difficult to detect. At present, there is no low-cost, convenient method that is sensitive enough to detect the amount of Gd that would be found in a typical sample of mouse plasma. Inductively-coupled-plasma mass spectrometry (ICP-MS) is sensitive enough, but expensive and slow. Relaxometry is less expensive, but insufficiently sensitive. Secondary labeling of GBCA for in vitro detection, has been used before, but has several undesirable effects. Radiolabeling requires specialized protocols and equipment. Fluorescent probes bleach, can significantly change the hydrophobic character of the contrast agent, and can affect the plasma kinetics and biodistribution. Fluorescent agents typically have poor biocompatibility, and only one has been approved for human clinical use. Finally, since fluorescent labels must be attached to the chelate, they are not measuring metal concentration directly, and will be inaccurate if decomplexation occurs. An alternative solution is the use of a sensitized chelator.

Sensitized chelators have been used for fluorescence applications for lanthanides for four decades. It has been observed that the addition of gadolinium to fluorescent europium or terbium compounds can enhance fluorescence output (Hemmila, *Scand J Clin Lab Invest*. 1988, 48(5): 389-399). The observed effect has been described in a number of ways: cofluorescene, fluorescence enhancement, and LRET. Fluorescence of sensitized lanthanide chelates is the result of a complicated energy transfer process. First, photonic excitation of the organic sensitizer causes electrons to jump to a higher-energy orbital. Some of these electrons drop back to the ground state by radiative decay: emitting a photon at the characteristic emission spectrum of the sensitizer. Another fraction of the population arrives at an excited triplet state through intersystem crossing. For suitable lanthanides, such as Tb or Eu, the energy from the ligand triplet can be transferred to the central lanthanide ion, which will then emit photons at the characteristic emission spectrum of the lanthanide (Li, et al., *Bioconjug Chem*. 1997, 8(2): 127-132). For Gd, the energy of the ligand triplet is typically insufficient to excite electrons in the metal, and the triplet will eventually return to the ground state by non-radiative decay (Yersin, *Transition Metal and Rare Earth Compounds III*, 2004, 241: 1-26).

The mechanism that underlies the emission of light from a sensitized lanthanide chelate was shown to be a function of the triplet level of the ligand, and the resonance level of the light-emitting metal (Crosby, et al., *Journal of Chemical Physics*, 1961, 34(3): 743). In fluorescent applications using organic molecules alone, both the intersystem crossing rate and the triplet radiative decay rate are sufficiently small that triplet deactivation is by non-radiative decay, and luminescence is only observed from the decay of the singlet excited state (Yersin, *Transition Metal and Rare Earth Compounds III*, 2004, 241: 1-26). But there is a photophysical interaction, the heavy ion effect, which underlies the observations of Crosby. Increased spin-orbit coupling between an organic-labeled ligand and a coordinated metal ion will increase the rate of intersystem crossing, and triplet radiative decay (McClure, *Journal of Chemical Physics*, 1949, 17(10): 905-913. If the central metal of the chelates is a lanthanide ion with a low-lying resonance level, such as Tb or Eu, it allows this triplet energy to be harvested, and released as metal luminescence.

The brightness, long fluorescent lifetime, and characteristically narrow emission bands of the sensitized lanthanide make it useful as a donor in fluorescent energy transfer applications (FRET) (Li, et al., *Bioconjug Chem*, 1997, 8(2): 127-132, and sensitized lanthanide chelates have found widespread use in biological applications. Since energy transfer from a donor occurs only at distances on the scale of nanometers, these systems are typically used to detect the proximity or binding of adjacent molecules or structures. (Hemmila, et al., *J Fluoresc*, 2005, 15(4): 529-542).

Not all lanthanides are equal for FRET systems. The lowest lying resonance level of Gd is higher than most organic ligands. As a result, Gd chelates have typically found a role as negative controls m studies of lanthanide fluorescence. However, it has long been recognized that the metastable triplet excited state of these chelates is localized to the organic ligand itself, it is not necessary for the metal ion to become excited (Crosby, et al., *Journal of Chemical Physics*, 1961, 34(3): 743; Freidzon, et al., 2011, 115(18): 4573. The implication is that even without the bright luminescence of a coordinated emitting lanthanide, a sensitized chelate may have a long-lived activated energy state, which can be manipulated to experimental advantage. The heavy ion effect of Gd was first shown by (Tobita, et al., *Journal of Physical Chemistry*, 1984, 88(13): 2697-2702) to facilitate phosphorescence from the triplet level of organic ligands without metal luminescence. More recently this effect was exploited to develop a Gd chelate that produces triplet emission in the near-infrared spectrum (Zhu, et al., *European Journal of Inorganic Chemistry*, 2011, (22): 3314-3320). In the same way that the heavy-ion effect can be used to elicit phosphorescence from an otherwise dark organic triplet, the detection of triplet phosphorescence from an otherwise dark organic label can be used to infer the presence of the metal ion.

Gd-DTPA (gadolinium-diethylenetriaminepentaacetic acid) is used clinically as a gadolinium based contrast agent (GBCA), one of a family of contrast agents that have become an indispensable component of diagnostic magnetic resonance imaging (MRI). GBCA shorten the relaxation time of nearby water protons, which manifests as an increased signal intensity in T1-weighted MRI. Originally introduced to provide an alternative to the perceived risks of iodinated contrast agents, CBCA have since been identified as contributing to the development of nephrogenic systemic fibrosis (NSF), which has led the FDA to require restrictive labeling for some previously approved agents (Penfield, et al., 2011, 24(5): 486). The ongoing evaluation of the safety of these agents, and the development of newer, safer GBCA, will require differentiation between chelated metal and free metal ion. The heavy ion effect depends on the development of spin-orbit coupling between the metal and the labeled chelator, that is, the complex must be intact to be detected.

All publications, patent applications, patents and other reference material mentioned are incorporated by reference in their entirety. In addition, the materials, methods and examples are only illustrative and are not intended to be limiting. The citation of references herein is not to be construed as an admission that the references are prior art to the present invention.

SUMMARY OF THE INVENTION

In a first aspect, the invention provides methods for detecting the presence of or the amount of a substantially non-emitting metal present in a sample by creating a compound that may arrive at a delectable excited state when bound to the substantially non-emitting metal. The methods further provide detecting the excited state of the substantially non-emitting metal by energy transfer to a second compound, which emits a signal when excited. In some instances, the substantially non-emitting metal may be gadolinium and the compound created may be cs124-DTPA. The substantially non-emitting metal and the compound created may be bound in the form of cs124-DTPA-Gd. In such instances, cs124 arrives at an excited triplet state in the presence of the substantially non-emitting metal for instance when excited by ultraviolet light. It may then be detected by energy transfer to a second compound such as, for instance, Terbium-DTPA. The first compound so created may be created, for instance, by providing an organic labeled chelate. Such may provide triplet excited states of different energy. In some instances, the second, signal emitting compound may be created without an organic labeled chelate, such as, for instance, Terbium-DTPA. In such instances, there may be no excited triplet state associated with the second compound. In other instances, the signal emitting compound may be created by, for instance, providing a different organic labeled cheltate that has a triplet excited state that is distinct from the organic labeled chelate of the first, non-emitting compound. A variety of detection systems may then be used based upon the energy of the excited triplet states of the first and second compounds and the emitting character of the second compound.

In some instances, the substantially non-emitting metal is a rare earth metal, for instance, a lanthanide, such as gadolinium (Gd), lanthanum, ytterbium, or lutetiumn, or any metal of the fifth or higher periods such as those having atomic numbers of 37 or higher. In some instances, the substantially non-emitting metal may exist in complex with a chelator, such as, for instance a gadolinium-based contrast agent (GBCA). In some instances, a light-absorbing sensitizer may be bound to the chelator. One exemplary sensitizer is, for instance, carbostyril124 (cs124). The second compound that emits a signal, such as for instance light, may be bound to the chelator of the first or may be a separate molecule, and the second compound that emits a signal, such as for instance light, may be a lanthanide, such as, for example, terbium (Tb) or europium (Eu).

In a second aspect, the invention provides methods for detecting the presence of a substantially non-emitting metal in a sample by a) providing a sensitizer to a chelator of the substantially non-emitting metal thereby creating a sensitized-metal complex; b) adding an unsensitized chelate, and c) detecting a signal from the unsensitized chelate. The concentration of the substantially non-emitting metal may be substantially proportional to the signal provided by the unsensitized chelate.

In some instances, the substantially non-emitting metal is a rare earth metal, for instance, a lanthanide, such as gadolinium (Gd), lanthanum, ytterbium, or lutetium, or any metal of the fifth or higher periods such as those having atomic numbers of 37 or higher. In some instances, the substantially non-emitting metal may exist in complex with a chelator, such as, for instance a gadolinium-based contrast agent (GBCA). In some instances, the sensitizer may be light-absorbing, and the sensitizer may be bound to the chelator. One exemplary sensitizer is, for instance, carbostyril124 (cs124). The unsensitized chelate may be a rare earth metal, for instance, a lanthanide, such as, for example terbium (Tb) or europium (Eu). The detecting a signal may be performed by, for instance, fluorescence, absorption spectroscopy, electron plasma resonance (EPR), nuclear magnetic resonance (NMR) and the like.

In some instances, the sensitizer and chelate may be conjugated to a phospholipid, and incorporated into a nanoparticle. In some instances, a fluorescent detector may be incorporated into the nanoparticle along with the sensitized chelate. In some instances the sample may be, for instance, a biological sample such as blood, plasma, urine, or cerebrospinal fluid.

In a third aspect, the invention provides methods for determining the amount of or concentration of a substantially non-emitting metal present in a sample by a) providing a sensitizer to a chelator of the substantially non-emitting metal thereby creating a sensitized-metal complex; b) adding an unsensitized chelate, and c) detecting a signal from the unsensitized chelate. The concentration of the substantially non-emitting metal may be substantially proportional to the signal provided by the unsensitized chelate.

In some instances, the substantially non-emitting metal is a rare earth metal, for instance, a lanthanide, such as gadolinium (Gd), lanthanum, ytterbium, or lutetium, or any metal of the fifth or higher periods such as those having atomic numbers of 37 or higher. In some instances, the substantially non-emitting metal may exist in complex with a chelator, such as, for instance a gadolinium-based contrast agent (GBCA). In some instances, the sensitizer may be light-absorbing, and the sensitizer may be bound to the chelator. One exemplary sensitizer is, for instance, carbostyril124 (cs124). The unsensitized chelate may be a rare earth metal, for instance, a lanthanide, such as, for example terbium (Tb) or europium (Eu). The detecting a signal may be performed by, for instance, fluorescence, absorption spectroscopy, electron plasma resonance (EPR), nuclear magnetic resonance (NMR) and the like.

In some instances, the sensitizer and chelate may be conjugated to a phospholipid, and incorporated into a nanoparticle. In some instances, a fluorescent detector may be incorporated into the nanoparticle along with the sensitized chelate. In some instances the sample may be, for instance, a biological sample such as blood, plasma, urine, or cerebrospinal fluid.

In a fourth aspect, the invention provides a kit for detecting the presence of or the amount of a substantially non-emitting metal present in a sample containing a sensitizer to a chelator of the substantially non-emitting metal. The kit may further contain one or more of instructions, one or more reagents, and one or more second chelate.

In some instances, the substantially non-emitting metal is a rare earth metal, for instance, a lanthanide, such as gadolinium (Gd), lanthanum, ytterbium, or lutetium, or any metal of the fifth or higher periods such as those having atomic numbers of 37 or higher. In some instances, the substantially non-emitting metal may exist in complex with a chelator, such as, for instance a gadolinium-based contrast agent (GBCA). In some instances, the sensitizer may be light-absorbing, and the sensitizer may be bound to the chelator. One exemplary sensitizer is, for instance, carbostyril124 (cs124). The second chelate may be a rare earth metal, for instance, a lanthanide, such as, for example terbium (Tb) or europium (Eu). The detecting may be performed by observing a signal by, for instance, fluorescence, absorption spectroscopy, electron plasma resonance (EPR), nuclear magnetic resonance (NMR) and the like. In some instances, the sensitizer and chelate may be conjugated to a phospholipid, and incorporated into a nanoparticle. In some instances, a fluorescent detector may be incorporated into the nanoparticle along with the sensitized chelate. In some instances the sample may be, for instance, a biological sample such as blood, plasma, urine, or cerebrospinal fluid.

BRIEF DESCRIPTION OF THE FIGURES

FIGS. 1A-1C describe labeled chelate synthesis and characterization.

FIG. 2 demonstrates fluorescent detection of cs124-DTPA-Gd with Tb-DTPA 90 μl Samples were prepared by serial dilution in PBS, 10 μl of 10 nM Tb-DTPA was added 10 minutes before reading. (a) In vitro results of fluorescence as a function of donor concentration. Typical data (open circles) was fit to the collision model (line) described in the text below in equation 1. Each point represents n=3 replicates, standard error bars are within symbol size. For an acceptor concentration of $1 \times 10^{-9}$ M, the predicted value of $\bar{n}_D = 4474 \pm 141.5$ nm$^3$ (±s.e.) L·mor$^1$. The critical statistic was derived from a 2-tailed Students t-test distribution giving $p<2 \times 10^{-16}$. The probability of electron transfer upon collision was determined to be 0.82±0.005694 (±s.e.) and the p-value was also $<2 \times 10^{-16}$.

FIGS. 3A-3D demonstrate the pharmacokinetics of cs124-DTPA-Gd. FIG. 3A: Plasma clearance of cs124-DTPA-Gd in the mouse. Individual plasma samples (open circles) were taken after a 7 minute equilibration period from n=5 C57B6 mice in which a clinical dose of cs124-DTPA-Gd had been infused. Samples were taken in rotation to minimize bias. Data were found to fit the bi-exponential model Equation 2 in the text. The characteristic distribution time of was found to be 13.2±0.543 min (mean±s.e.), with $p=2 \times 10^{-16}$, and the elimination time 92.2±11.7 min (mean±s.e.) with $p=5.49 \times 10^{-8}$. These times correlate closely to the manufacturers data for Magnevist®, 12.2±7.8 min (mean±s.d.) and 96.0±7.8 min (mean±s.d.) respectively.

DETAILED DESCRIPTION OF THE INVENTION

Before the present methods are described, it is to be understood that this invention is not limited to particular methods and experimental conditions described, as such methods and conditions may vary. It is also to be understood that the terminology used herein is for purposes of describing particular embodiments only, and is not intended to be limiting, since the scope of the present invention will be limited only by the appended claims. As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth in their entirety.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference I their entireties.

Definitions

The terms used herein have the meanings recognized and known to those of skill in the art, however, for convenience and completeness, particular terms and their meanings are set forth below.

"Agent" refers to all materials that may be used to prepare a composition, including, for instance, pharmaceutical and diagnostic compositions, or that may be compounds such as small synthetic or naturally derived organic compounds, nucleic acids, polypeptides, antibodies, fragments, isoforms, variants, or other materials that may be used independently for such purposes, all in accordance with the present invention.

"Analog" as used herein, refers to a chemical compound, a nucleotide, a protein, or a polypeptide that possesses similar or identical activity or function(s) as the chemical compounds, nucleotides, proteins or polypeptides having the desired activity or effect of the present invention, but need not necessarily comprise a compound that is similar or identical to those compounds of the preferred embodiment, or possess a structure that is similar or identical to the agents of the present invention.

"Derivative" refers to the chemical modification of molecules, either synthetic organic molecules or proteins, nucleic acids, or any class of small molecules such as fatty acids, or other small molecules that are prepared either synthetically or isolated from a natural source, such as a plant, that retain at least one function of the active parent molecule, but may be structurally different. Chemical modifications may include, for example, replacement of hydrogen by an alkyl, acyl, or amino group. It may also refer to chemically similar compounds which have been chemically altered to increase bioavailability, absorption, or to decrease toxicity. A derivative polypeptide is one modified by glycosylation, pegylation, or any similar process that retains at least one biological or immunological function of the polypeptide from which it was derived.

A "small molecule" refers to a molecule that has a molecular weight of less than 3 kilodaltons (kDa), preferably less than about 1.5 kilodaltons, more preferably less than about 1 kilodalton. Small molecules may be nucleic acids, peptides, polypeptides, peptidomimetics, carbohydrates, lipids or other organic (carbon-containing) or inorganic molecules, as those skilled in the art will appreciate. A "small organic molecule" is normally an organic compound (or organic compound complexed with an inorganic compound (e.g., metal)) that has a molecular weight of less than 3 kilodaltons, and preferably less than 1.5 kilodaltons, and more preferably less than about 1 kDa.

"Subject" or "patient" refers to a mammal, preferably a human, in need of or undergoing treatment or screening for a condition, disorder or disease.

"Non-emitting" or "substantially non-emitting" as used herein means non-fluorescent or substantially non-fluorescent, or non-light emitting, or substantially non-light emitting, in any range from UV to IR General Description The present methods provide a sensitive, convenient, and cost effective method to detect low concentrations of gadolinium based contrast agents (GBCA). The present methods include adding a sensitizing molecule to the GBCA, and using a detecting reagent for fluorescent reading.

Gadolinium (Gd) belongs to the lanthanides, a family of rare-earth elements. GBCA are formed by the complexation of Gd with a chelator. If a light-absorbing "sensitizer" is covalently bound to the chelator, some lanthanides, such as terbium (Tb) and europium (Eu), display luminescent properties. That is, they will emit light if exposed to the excitation wavelength of the sensitizer, and they have been used as energy donors in luminescence resonance energy transfer (LRET) applications. GBCA are not sensitized, and are non-luminescent, and therefore have not been used before for fluorescence or LRET. In addition, sensitized chelates of gadolinium, in solution, are non-luminescent.

The present methods use existing methods to attach a sensitizer to the chelator of the GBCA, to create a sensitized-GBCA (s-GBCA) and detect the concentration of the complex by the addition of a trace amount of unsensitized chelate, such as, for example Tb chelate. The fluorescent signal from the resulting complex (e.g. Tb complex) is directly proportional to the concentration of s-GBCA, and independent of the concentration of the unsensitized chelate, e.g. Tb. The mechanism behind this signal may be energy transfer or transmetallation. Previous lanthanide FRET work has all used light-emitting metals, and the triplet-emitter work has all been done in the solid state for light emitting diodes (LED).

The concentration of s-GBCA in solution may be determined by absorption spectroscopy down to $1^{-3}$M using the molar extinction coefficient of the sensitizer, s-GBCA has magnetic and biological characteristics that are identical to the original GBCA and may be used directly for MR experiments. Blood samples may be withdrawn from the animal at time intervals appropriate to the experiment at hand, whereupon the detector molecule is added, and the concentration of the non-fluorescent metal is read in a fluorescent plate reader. Detection sensitivity of s-GBCA in the plate reader is on the order of $1^{-7}$M.

When the GBCA is incorporated in a dendrimer or nanoparticle, the Tb signal may be used similarly to LRET to evaluate the size and composition of the nanoparticle. This agent and method may be used in a small animal experimental model, as it provides a method sufficiently sensitive to measure the concentration of GBCA in small plasma sample volumes.

The methods described herein provide the following: i) an improvement over previous methods in sensitivity and convenience of measurement of contrast agents in small animal imaging; ii) a method for obtaining a measureable signal from a non-fluorescent or weakly-fluorescent metallic complex; iii) an application to generate aFRET signal from s-GBCA to a non-sensitized lanthanide chelate; iv) a formulation of a spin-label: v) a method to elicit and detect a change in the electronic configuration of an MR contrast agent; vi) a method to elicit and detect a change in the electronic configuration of an injected complex by infrared excitation and emission; vii) a formulation of a photoactivable chelator conjugated to a phospholipid; viii) incorporation of the photoactivable phospholipid-chelator in a nanoparticle, and a method to detect nanoparticle integrity and composition In some instances the methods provide conjugation of carbostyril124 (cs124) to Gadolinium-DTPA (the commercial GBCA Magnevist®). The resulting compound has a well defined absorption spectrum in water with maxima at 328 nm and 341 nm. When the sample containing cs124-Gd-DTPA is excited at 341 nm, the characteristic emission spectrum of Tb can be detected by time-resolved fluorescence on a fluorescent plate reader, and is proportional to the concentration of Gd. The clinical dose of Magnevist may be $1^{-4}$ mol per kg body weight, with a distribution half-life of 12 minutes, and a plasma clearance half-life of approximately 81 min. Typical plasma concentrations range from $6.0^{-4}$ M at 3 min post injection, to 2.44 M at 60 minutes post injection. When sensitized, the compound can be detected on a standard laboratory fluorescence plate reader at $2.5^{-7}$ M in a volume of 100 mL, allowing accurate detection from a plasma sample volume of 1 mL at 60 minutes post injection, and can be detected from undiluted samples up to 4 hours post injection. This is in contrast to relaxometry which requires a 200 mL plasma sample and is at the limit of detection for time points longer than 1 hour. Plasma samples are diluted in a buffer containing a non-sensitized chelate of Terbium.

In some instances, different sensitizers and different chelators may be provided. In some instances a contrast agent may be provided where the concentration may be detected by Electron Plasma Resonance (EPR). In such a system, the agent may function as a spin-label. In some instances the concentration may be detected by nuclear magnetic resonance (NMR). In such a system, the photo-excited state can be differentiated from the ground state of the complex by a change in magnetic resonance. In some instances, the composition may be provided so as to shift the excitation and emission wavelengths, particularly in the infrared region. In addition to Gadolinium, Lanthanum, Ytterbium. and Lutetium also have stable 4f electron configurations, and as a result, do not have low-lying energy states that allow fluorescent emission by an excited sensitized chelate. The choice of an organic dye may be made so as to allow excitation by infrared radiation (IR). The long-lived excited state of the complex will be at a lower-energy level, that is, one farther infrared Detection of this complex may be made by energy transfer to an appropriate infrared fluorescent species such as Europium or Cerium or by EPR or NMR. The complex thus formed may be both excited and detected by infrared radiation, thereby allowing whole-animal imaging by infrared detection, or allowing the initiation of excited EPR or NMR states during experiment by infrared radiation.

In some instances, the sensitizer and chelate may be conjugated to a phospholipid. This molecule may be incorporated into nanoparticles for imaging such as is described in, for example, Fisher et. al., U.S. Pat. No. 7,947,307, the disclosure of which is herein incorporated by reference, and used to detect and quantify the concentration of the nanoparticle contrast agent. In some instances, the fluorescent detector may be incorporated into the nanoparticle along with the sensitized chelate, which can be used to quantify the concentration of the sensitized chelate. Since the fluorescent energy transfer does not occur across large distances, this also indicates that the nanoparticle is intact.

These methods allow for the rapid measurement of plasma kinetics parameters of s-GBCA formulations, using a standard laboratory fluorescent reader equipped for time resolved fluorescence. Currently, GBCA is measured by relaxometry, which has low sensitivity, requiring large sample volumes, or ICP-MS, which is expensive and time consuming. The present methods reduce experimental costs, facilitate efficient screening protocols, reduce experimental variability, and reduce the number of animals required for experimentation.

Determination of plasma kinetics parameters requires the collection of serial samples from a single test subject, at concentrations as low as 10 nM. For a blood sample of 50 µL or less, a typical volume for a mouse study, the only option is ICP-MS. Alternatively, in relaxometry, larger volume requirements preclude serial sampling in small animals.

Current FRET and LRET systems using metal donor-acceptor detection systems can use only fluorescent donors and fluorescent acceptors. The present methods describe fluorescent detection of non-fluorescent donors.

Recognizing the need for alternative testing modalities for GBCA, in 2011 BioPAL introduced a 96-well format colonmetric ELISA assay which purports to measure a GBCA excreted in urine by reaction with rabbit antiserum raised against Gd-DTPA. This kit can only be used for urine testing, not for plasma. The present methods are less expensive to manufacture, more sensitive, specific for Gd content, and may be used for plasma studies.

The present methods expand the utility of existing CA. The sensitizer can be conjugated directly to an existing FDA-approved GBCA, allowing direct detection of the compound. At present, there is no GBCA which can be directly detected by fluorescence.

The high sensitivity of the present methods also means that plasma samples may be further diluted, allowing the use of standard size exclusion chromatography methods of plasma lipoprotein research for characterization of particle plasma biodistribution.

The present methods solve the problem of quantifying, rather than merely detecting GBCA. In the present methods, the excited state is maintained on the donor complex only, which is in solution, and physically separated from the acceptor. A related method termed "co-fluorescence" relies on the formation of solid crystal aggregates of donor and acceptor, making it quantitative only the concentration of acceptor. The present methods also avoid the problem of spectral bleed through, in which the donor fluorescent signal must be subtracted from the acceptor signal.

When the sensitized chelate is on a phospholipid, and incorporated into a nanoparticle, the present methods solve the problem of determining the labeling efficiency of the nanoparticle synthesis process. The observation and quantification of emitted light from this system can be used to determine a) the concentration of the donor complex, b) the integrity of the nanoparticle, and c) the size of the particle.

The present methods also provide a way to determine if particle components remain associated with the nanoparticle, or dissociate over time. There is currently no direct method to do this.

The present methods provide many advantages in the field of small animal experimentation in GBCA. Animal labs that use GBCA for angiography in neurology, nephrology, cardiology, oncology, and other research areas are now able to accurately measure GBCA concentrations at any experimental time point, with a turnaround of minutes. This allows for rapid identification of GBCA delivery and clearance, and allow for real-time adjustment of experimental conditions.

The present methods may be used to measure the concentration of GBCA on nanoparticles such as those described by Fisher et al., U.S. Patent Publication 2006/0099148, the disclosure of which is incorporated herein by reference in its entirety, such as those used for atherosclerosis MRI studies. There is currently no fluorescence-based method to do this.

Figure 1A:
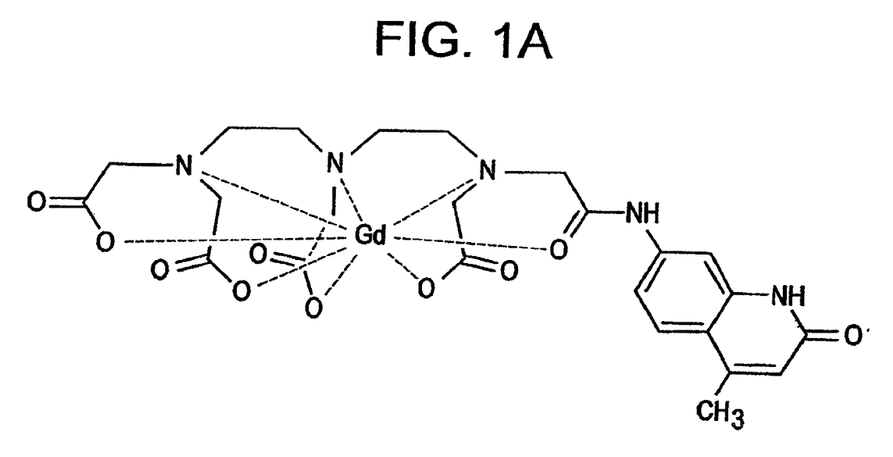
FIG. 1A: Schematic diagram of cs124-DTPA-Gd.
Figure 1B:
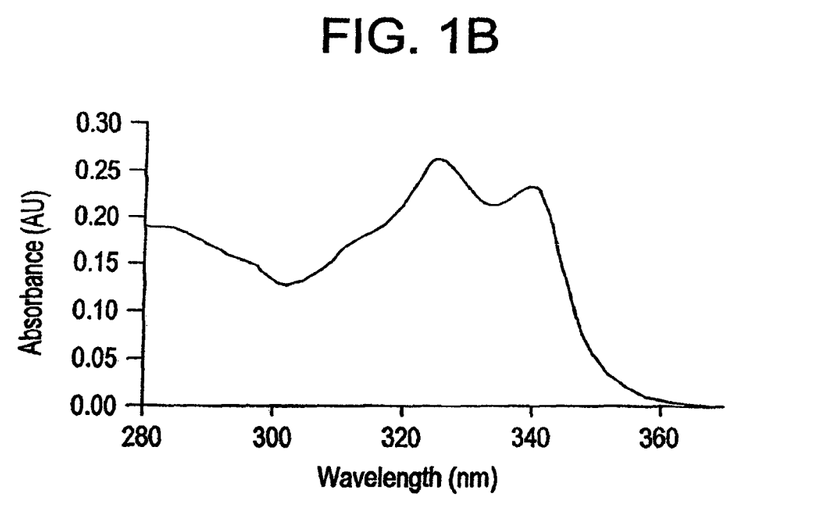
FIG. 1B: The absorption spectrum of the labeled chelate is characteristic for cs124-DTPA, with maxima at 328 and 341 nm.
Figure 1C:
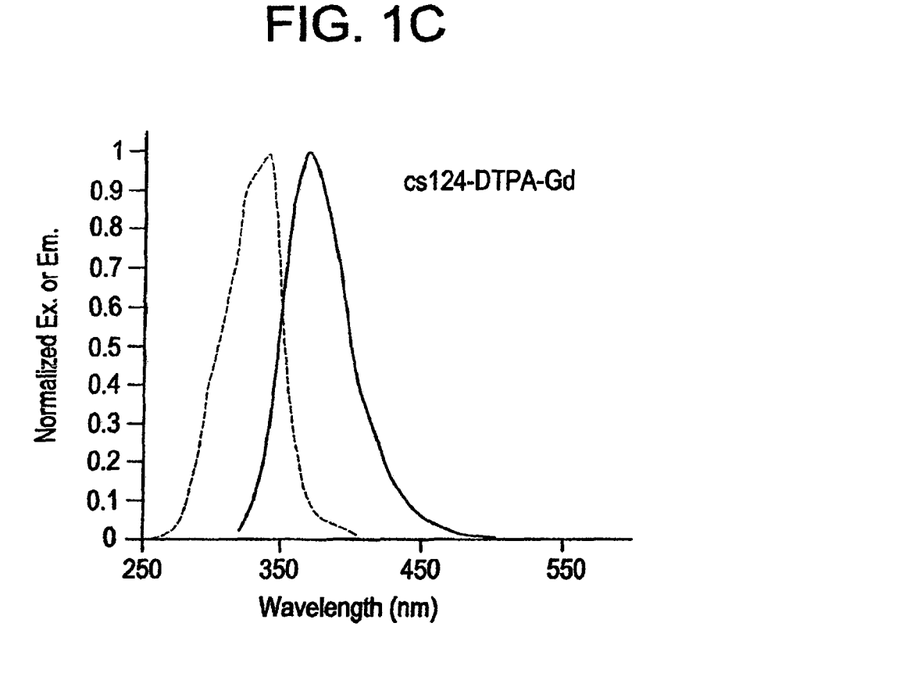
FIG. 1C Excitation and emission spectrum of cs124-DTPA-Gd, showing no luminescence from Gd, and no luminescence in the characteristic spectrum of Tb.

The present methods have broad applicability in physical chemistry for the detection of small quantities of ionic metals. It also has broad applicability in nanomedicine, for nanoparticle compositional analysis, to identify the presence and concentrations of two or more target molecules on the same nanoparticle Synthesis and Characterization of cs124-DTPA-Gd Synthesis follows the method of (Li, et al., *Bioconjug Chem*, 1997, 8(2): 127-132). FIG. 1(a) shows the chemical structure of cs124-DTPA-Gd. Conjugation of multiple dye molecules resulting in DTPA-cs124$_2$ is unlikely, as only one HPLC peak was seen. Unconjugated cs124 in aqueous solution has a characteristic excitation peak at 341 nm, with a lower shoulder at 306 nm. Successful synthesis of cs12-DTPA is indicated by the characteristic absorption spectrum in FIG. 1(b), with a right shift of the highest energy peak to 328 nm with higher absorption than the peak at 341. Tb emission when complexed with unsensitized DTPA was on the order of background signal, and without cs-124 absorption peaks. Tb with cs124 alone showed no Tb fluorescence. The time resolved fluorescence of Tb increased linearly as increasing amounts of Tb were added to the chelate, and reached a saturation plateau, allowing determination of the molar extinction coefficient of the metal chelate to be $1.07E4$ $M^{-1}$ $cm^{-1}$. When complexed with Gd, cs124-DTPA showed the same characteristic absorption as with Tb, and emission at the characteristic wavelength for cs124, but no lanthanide fluorescence. These results show successful synthesis of the component molecules for s-GBCA detection, a sensitized Gd chelate, and an unsensitized Tb chelate, each of which has no time-resolved fluorescence signal when in solution alone.

The relaxivity of cs124-DTPA-Gd was the same as that of DTPA-Gd, showing a decrease in r1 relative to $Gd^{3+}$. Size and diffusivity, as revealed by dynamic light scattering (DLS) were similar although sensitized chelates are, predictably, slightly larger than unsensitized chelates. Shown in Table 1.

TABLE 1

Physical properties of the experimental and reference compounds.

| Compound | Diffusivity D ($cm^2/s$) | Absorbance and Fluorescence | | | Relaxivity r1 ($M^{-1}$ $ms^{-1}$) |
| --- | --- | --- | --- | --- | --- |
| | | $A_{max}$ (nm) | $Ex_{max}$ (nm) | $Em_{max}$ (nm) | |
| DTPA-Tb | $3.5 \times 10^{-6}$ | 280 | 300 | 365 | — |
| cs124 | — | 328 | 310 | 370 | — |
| cs124-DTPA-Gd | $2.5 \times 10^{-6}$ | 328 | 341 | 375 | $3.32 \pm 1.4$ |
| Magnevist ® | — | — | — | — | 3.4 |
| Gd3+ | $8.0 \times 10^{-6}$ | — | — | — | $9.16 \pm 0.96$ |

When xylenol orange coordinates $Gd^{3+}$ ion, absorption at 573 decreases relative to that at 433. Samples of cs124-DTPA-Gd, incubated with 50 mM xylenol orange show that free $Gd^{3+}$ is detectable when the concentration of the chelated complex is above 1.75 mM, indicating a free ion concentration of 0.06%.

In Vitro Detection of Sensitized Gadolinium Chelates

Figure 2:
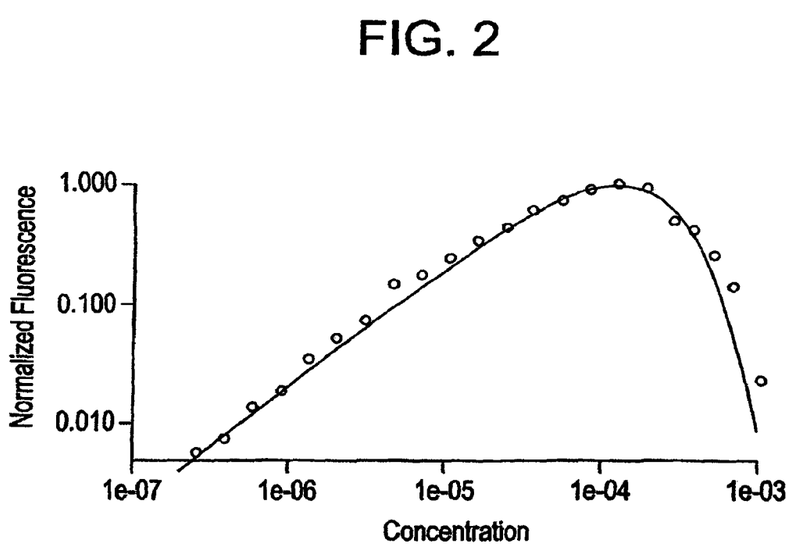

To assess the ability of DTPA-Tb to generate a fluorescent signal when in solution with cs124-DTPA-Gd, a fluorescent plate reader capable of detecting the integrated fluorescent signal from 600 to 2100 μs was used. The concentration of cs124-DTPA-Gd was determined by absorption spectroscopy, and dilutions of the complex from $10^{-2}$ to $10^{-10}$ were placed in a black 96 well plate. $10^{-9}$M of DTPA-Tb was added to each well and excited at 341 nm. The integrated signal was read at 545 nm. Evaluation of Tb fluorescence showed that the time-resolved Tb signal was a function of the concentration of Gd, demonstrating a marked quenching effect at concentrations higher than $10^{-3}$M, shown in FIG. 2

To determine the stability of the chelate in solution as a function of time, readings were made at different time points. If there is an exchange of Tb with Gd on the sensitized chelate, then a dramatic increase in signal should be observed. The intensity of cs124-DTPA-Tb is 10000 fold higher than the equivalent concentration of cs124-DTPA-Gd. No significant change of intensity was observed at 5, 30, and 60 minutes, indicating that exchange of metals between sensitized and unsensitized chelates was undetectable during the time course of the experiment.

In Vivo Detection of Sensitized Gadolinium Chelates

Figure 3A:
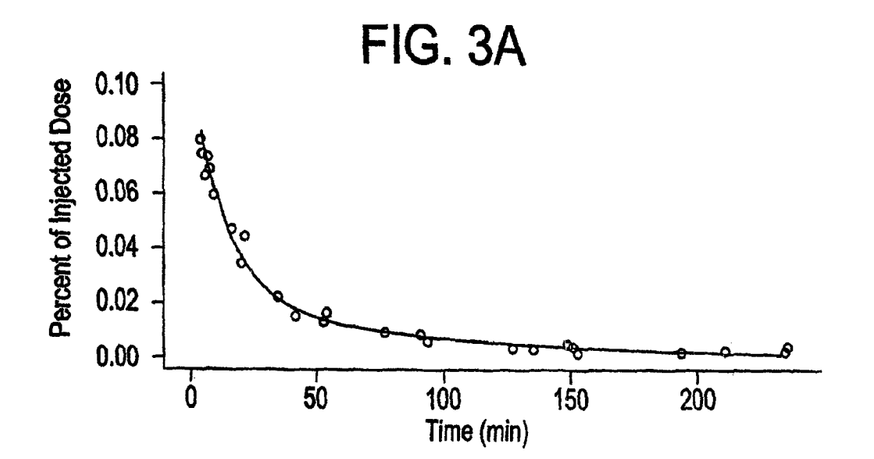
Figure 3B:
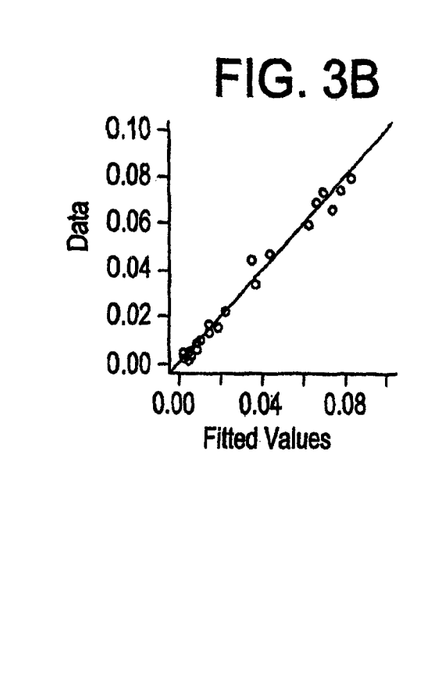
FIG. 3B: Data plotted against fitted values shows a close correlation, with the solid line representing perfect fit.
Figure 3C:
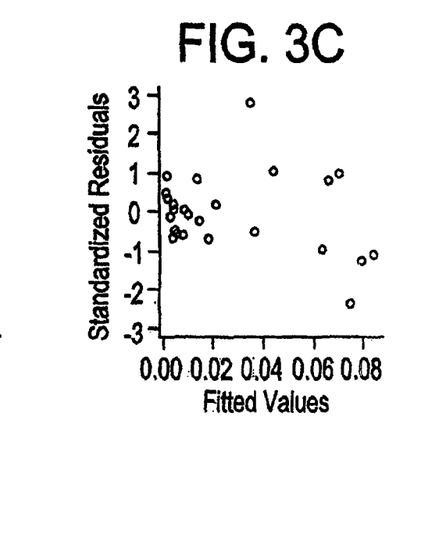
FIG. 3C: Standard residuals plotted against predicted values shows no trend in the variance of the data with predicted value.
Figure 3D:
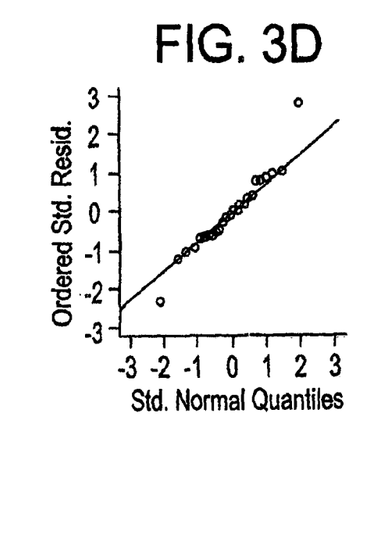
FIG. 3D: Standard residuals plotted against theoretical normal quantiles shows that errors are normally distributed. The residual s.e. is 0.003447 on 23 d.f.

To evaluate the in vivo properties of cs124-DTPA-Gd quantification accuracy in whole body experiments, five C57-Black6 mice were given metered injections of 0.1 mmol/kg, the clinical dose for Magnevist, via the saphenous vein, and allowed a 7-minute time period for uniform plasma distribution. To determine the pharmacokinetic parameters, 50 μL blood samples were taken from each mouse so that no more than 200 μL total blood volume was removed from a single mouse during the experiment. Sampling time points were arranged so that time points were sequential, with the average time between points being 3 minutes for the first 30 minutes, and 10 minutes for the remainder of the experiment, up to 2 hours. Blood was centrifuged at 13000×g for 5 minutes, and approximately 25 μL of plasma isolated from each sample. Of these samples, 101 μL was diluted in 100 μL deionized water containing 10M DTPA-Tb, and read according to the in vitro protocol, against a standard curve of known concentration. The results, shown in FIG. 3a, were fit to a bi-exponential equation describing the standard 2 compartment open mamillary system used for plasma clearance evaluation. Twenty-four data points were used to generate a best-fit curve The characteristic distribution time was determined to be 14 minutes, and the elimination time 90 minutes, which corresponds closely to the kinetic parameters published in the package insert for Magnevist. (b) Data plotted against fitted values shows a close correlation, with the solid line representing perfect fit. (c) Standard residuals plotted against predicted values shows no trend in the variance of the data with predicted value. (d) Standard residuals plotted against theoretical normal quantiles shows that errors are normally distributed. The residual s.e. is 0.003447 on 23 d.f.

In Vivo Imaging

Figure 4:
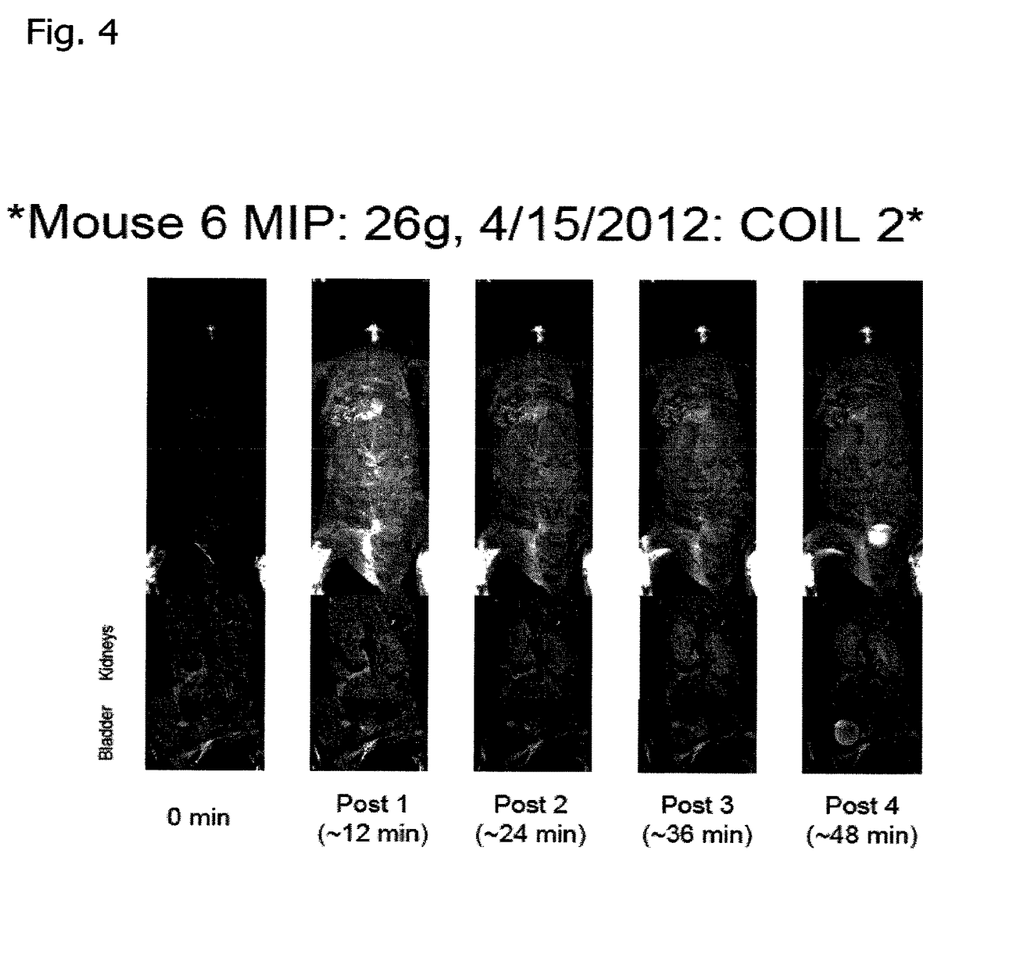
FIG. 4 provides the maximum intensity projections for c57-Black6 mice that were injected as for clearance studies and imaged in a custom small-animal coil to evaluate the imaging efficacy of the sensitized contrast agent.

To evaluate the imaging efficacy of the sensitized contrast agent, c57-Black6 mice were injected as for clearance studies, and imaged in a custom small-animal coil. Maximum intensity projections are shown in FIG. 4.

Discussion

Small animal studies form the bulk of experimental innovation in contrast media GBCA are currently the most effective clinical agent, and offer the clearest route to translational applications. The introduction of a sensitive and convenient method for quantification will allow the leaders in innovation to perform rapid pharmacokinetic studies and provide a new standard for in vivo screening. The data demonstrate that a sensitizing the chelator used in the formulation of GBCA can allow quantitative detection of the concentration of metal with minimal alteration of the characteristic imaging and pharmacokinetic properties of the agent. In future work, systematic analysis of the effect of varying sensitizer and chelate may reveal new applications of this system.

EXAMPLES

The following examples are set forth to provide those of ordinary skill in the art with a description of how to make and use the methods and compositions of the invention, and are not intended to limit the scope thereof. Efforts have been made to insure accuracy of numbers used (e.g., amounts, temperature, etc.) but some experimental errors and deviations should be accounted for. Unless indicated otherwise, parts are parts by weight, molecular weight is average molecular weight, temperature is in degrees Centigrade. and pressure is at or near atmospheric.

Example 1

Sensitized Chelate: Synthesis and Characterization

Cs124-DTPA (FIG. 1A) was prepared by incubation of precursor materials.

Chelation Studies: Comparison of Chelation Affinity by Fluorescence and Xylenol Orange Absorption and fluorescence experiments were conducted on a SpectraMax M5 plate reader (Molecular Devices, Sunnyvale, Calif.). For fluorescence, the excitation source was a xenon flash lamp with monochromators employed to tune excitation and emission wavelengths. Automatic cutoff filters were used for all emission and excitation spectra. The excitation maximum for cs124 is 341 nm, 9 nm excitation and 15 nm emission slits were used. For time resolved fluorescence (TRF), a delay time of 600 μs and an integration time of 1000 μs were used. Peak fluorescence at 545 nm and 485 was recorded.

The white powder from lyophilization was suspended in 1 mL deionized water and stirred for 1 hour at RT, with occasional sonication to disperse observed aggregates. The solution was filtered in a 10 kD MWCO filter (Millipore) and the absorption spectrum measured between 250 and 450 on a nanodrop (Thermo Scientific). Concentration was determined by using the Beer-Lambert Law Abs=εCl, where ε is the molar extinction coefficient, l is the path length, and C is concentration. The molar extinction coefficient for cs124-DTPA-Ln was determined by diluting a sample with a known absorption value over 3 orders of magnitude, titrating in increasing amounts of $Tb^{3+}$, and measuring the increase in Tb emission. A linear increase in emission was observed that reached a plateau. The point of intersection between the linear increase and plateau marks the concentration at which all chelation sites are occupied. Plotting the ratio $Abs_{(341)}$cs124-DTPA:Tb concentration v. fluorescence, gives c(cs124-DTPA-Tb)=$1.07 \times 10^4$ $M^{-1}$ $cm^{-1}$. It is assumed that, since all lanthanides have extremely small absorption cross-section, the extinction coefficient is the same for all cs124-DTPA chelates.

For determination of free $Gd^{3+}$ in solution after chelation. 3 mg xylenol orange was dissolved in 50 mM acetic acid pH 5.8, and 90 μL added to each well of a clear 96 well plate. Triplicate samples of 10 μL $10^{-3}$M cs124-DTPA were added to each well, and increasing amounts of $Gd^{3-}$ titrated in. Absorption was read at 573 and 433, against a standard of known $Gd^{3+}$ concentration.

The stock solution was diluted to $10^{-3}$M and absorption of a 1:1000 dilution measured at 328 and 341 nm to confirm concentration. In a clear 96 well plate, cs24-DTPA was provided In Vitro Detection Studies The concentration of cs124-DTPA-Gd was determined by absorption spectroscopy, and samples diluted to $5 \times 10^{-3}$M, pH 7.4. Triplicate samples were placed in a black 96-well plate, and serial dilutions prepared to $1 \times 10^{-9}$M, in 1001 μL deionized water. 10 μL of $1 \times 10^{-9}$M DTPA-Tb was added to each well, and incubated for 10 minutes. The plate was read as for the chelation studies. A 1:1 molar ratio of Gd3+ was added to each well, and incubated for 30 minutes, and read.

Derivation of Model:

Both the donor and acceptor are free to diffuse by Brownian motion throughout the solvent, and whenever the distance of closest approach between two particles is small enough that it is possible for a transfer to occur, we define a collision. The result of this collision is either a success, if a transfer, or a failure if no transfer. The fluorescence of a single acceptor will be proportional to the total number of successful transfers to it from colliding donors. We write $$F = \alpha \bar{n}_f \quad (S1)$$

where $\alpha$ is the fluorescence yield per collision, and $\bar{n}_f$ is the average total number of successful collisions per acceptor in $t_e$. We define the average number of collisions per particle within the experimental time $t_e$ as $\bar{n} = \bar{n}_D + \bar{n}_A$, the sum of the average number of donor collisions $\bar{n}_D$ and acceptor collisions $\bar{n}_A$. Since some donors will return to the ground state before they encounter an acceptor, and since acceptor-acceptor collisions are not fluorescent, $\bar{n}_f < \bar{n}$. We note that each collision is a Bernoulli trial, with a probability of success p, which allows us to define $\bar{n}_f$ in terms of $\bar{n}$. When a donor collides with an acceptor at the kth collision, the likelihood of transfer will then rest upon two things: the probability of failure in the previous (k−1) collisions, $(1-p)^{(k-1)}$, and the probability of success in the current collision, p. This is the geometric distribution $Pr(X=k)=(1-p)^{(k-1)}p$, and it describes the probability of success on the kth collision for a given donor. From this we can write $$\bar{n}_f = \bar{n}_D (1-p)^{(\bar{n}-1)} p \quad (S2)$$

and substituting into Equation S1:

$$F(\bar{n}) = \alpha \bar{n}_D (1-p)^{\bar{n}-1} p \quad (S3)$$

Upon normalization by a, we obtain Equation 1.

$$\hat{F}(\bar{n}_D) = \frac{F(\bar{n}_D)}{\alpha} = \bar{n}_D (1-p)^{\bar{n}-1} p \quad (1)$$

All that remains is to determine the number of donor and acceptor collisions. We start with a number concentration of particles P composed of donor D and acceptor A:

$$\frac{N_P}{V} = \frac{N_D + N_A}{V} \quad (S4)$$

where $N_i$ is number of the respective species and V is the total volume. The rate of collision per unit volume can be expressed as $$\frac{N_C^V}{V} = \frac{N_P^2}{V^2} \sigma_P \sqrt{2}\, \bar{v} \quad (S5)$$

where $\sigma_P = (2d)^2/4$ is the collisional cross section, for a particle of diameter d, $\bar{v}$ is the average velocity, and $\sqrt{2}$ is a scaling factor to account for the random orientation of the velocity vectors. The total number of collisions per unit volume in $i_c$ is.

$$\frac{N_C}{V} = \frac{N_P^2}{V^2}(\sigma_P \sqrt{2}\, \bar{v} t_e) \quad (S6)$$

The quantity in parentheses defines an interaction volume. $V_C = \sigma_P \sqrt{2} \bar{v} t_e$, swept out by a single particle during the experiment. This allows us to write the average number of collisions per particle as a function of the interaction volume:

$$\bar{n} = \frac{N_C}{N_P} = \frac{N_P}{V}(\sigma_P \sqrt{2}\, \bar{v} t_e) = \frac{V_C}{V}(N_D + N_A) \quad (S7)$$

we can see that the number of donor collisions is $\bar{n}_D = N_D \cdot V_C \cdot V^{-1}$, and the number of acceptor collisions is $\bar{n}_A = N_A \cdot V_C \cdot V^{-1}$. Substituting into Equation S4 gives $$\bar{n} = \bar{n}_D + \bar{n}_A = \gamma V_C (C_D + C_A) \quad (S8)$$

where $C_D$ and $C_A$ are the molar concentrations of donor and acceptor, respectively, and $\gamma = 6.022 \times 10^{26}$ L·m$^{-3}$·mol$^{-1}$ is a unit conversion constant. Substituting into Equation 1 gives the normalized fluorescence distribution as a function of donor concentration:

$$\hat{F}(C_D) = \theta V_C C_D (1-p)^{\gamma V_C (C_D | C_A) 1} p \quad (S9)$$

for a fixed concentration of acceptor $C_A$. For low concentration, where the interparticle distance is greater, the chance of transfer to an acceptor is proportional to the chance of collision, i.e the number of donors per acceptor. As the concentration of donor increases, the number of transfers to an acceptor increases, but the per-donor chance of transfer to another donor also increases, eventually becoming more likely than the probability of transfer to an acceptor, as observed in experiment.

In Vivo Plasma Kinetics Studies

All animal procedures were approved by the NYU Institutional Animal Care and Use Committee. C57-Black6 mice were anesthetized by isofluorene inhalation, and the hair removed from the anterior surface of the left hindlimb to reveal the superficial saphenous vein. A microcannula formed from #10 polyeurethane tubing was prepared by heating then stretching the tubing. The caudal end of the microcannula was attached to a 1 mL tuberculin syringe, and the distal end inserted into the saphenous vein. A total of 54 μL of contrast agent was infused via syringe pump at a rate of 50 μL/min. After the infusion was stopped, the cannula was removed and the site of cannulation sealed with a cyanoacrylate adhesive. A recovery time of 7 minutes was allowed to ensure uniform plasma distribution and to allow the animal to regain normal functioning. Also at this time, a local anesthetic (proparacaine) was applied to both eyes. 5 μL heparin PBS (10 U/mL) was introduced to one end of a 50 μL borosilicate glass microcapillary tube (Fisher), and blood samples were withdrawn from the retro-orbital plexus of awake mice at measured intervals. Blood was centrifuged at 13000×g for 5 minutes, and 25 μL of plasma recovered from the sample. 10 μL of each plasma sample was evaluated as in the in vitro detection method, against a known concentration diluted in an equal concentration of heparinized PBS and control mouse plasma (no contrast agent infusion).

Mathematical Modeling of Plasma Clearance

The solution of the transport equations that describe concentration as a function of time for a two-compartment open mamillary system is the bi-exponential equation $$C(t) = A e^{t/\tau_a} + B e^{t/\tau_b} \quad \text{Equation 2}$$

Where C it concentration, t is time, A and B are the initial concentrations of each compartment, and $\tau_a$ and $\tau_b$ are the characteristic times for compartments A and B respectively. Plasma kinetics of most GBCA can be described by this equation. Data was linearized by taking the natural logarithm of the concentration, and a least-squares method was employed to find the coefficients of equation 2. Goodness of fit was determined by the combined Pearson's R-squared value. Normalized residuals were plotted against predicted quantiles of a normal distribution to determine if measurement errors are normally distributed relative to the model, using built in libraries of the R statistical programming language.

Example 2

Background

The use of gadolinium-based contrast agents (GBCA) is integral to the field of diagnostic magnetic resonance imaging (MRI). Strategies to combine fluorescent detection with MRI have relied on bifunctionalized particles, conjugating a fluorescent element and a magnetic contrast agent on the same compound. However, most multi-modal compounds are not designed to demonstrate a coupled effect between the two detection methods. By exploiting the heavy-ion effect, we developed a compound that maintains a nonemittive excited triplet state on a fluorescent label only in the presence of chelated Gadolinium. The nonemittive triplet allows the compound to become a "dark donor," transferring energy to a second, fluorescent, detector molecule. The compound, carbostyril-124-diethylenetriaminepentaacetic acid-Gadolinium (cs124-DTPA-Gd), can be quantified on a standard laboratory plate reader, with a lower limit of detection of 10-7 M.

Results

We examined the effect of single and double cs124 labels on detection sensitivity. In fluorescent applications that consist of only organic molecules, both the intersystem crossing rate and the triplet radiative decay rate are small, and luminescence is observed only from the decay of the singlet excited state. However, increased spin-orbit coupling between an organic-labeled chelate and a coordinated heavy metal ion increases the rate of intersystem crossing, enriching the lowest triplet energy level of the organic label. For small interparticle distance, R, this triplet energy can transfer to another molecule by non-radiative electron exchange.

We showed that this energy transfer can be made to a fluorescent acceptor molecule, and used to detect the presence of the GBCA in tissue. Conversely, identification of the location of the GBCA by MRI identifies a region of tissue to which energy transfer can be stimulated by directed fluorescent excitation. One drawback to this technique is that efficiency of energy transfer attenuates for high concentrations of donor. We demonstrated that increasing the number of organic labels can correct this problem. For a donor with a single organic label, the probability of transfer is proportional to the probability of the first collision being between a donor and an acceptor, and decreases sharply with high concentration as donor-donor collisions become dominant. A donor with two organic labels may sustain an excited triplet state for a second collision, thereby increasing the fluorescent signal of the acceptor even for high concentrations of donor.

The invention claimed is:

1. A method for detecting presence of or amount of a substantially non-emitting metal in a solution comprising:
   a) binding a first compound to the substantially non-emitting method in the solution to form a complex that is substantially non-emitting;
   b) exposing the substantially non-emitting complex to a source of illumination to cause the first compound to enter into an excited state while the metal in the complex remains substantially non-emitting;
   c) contacting the illuminated complex in the solution with a second compound;
   d) detecting energy transferred to the second compound from the excited state of the first compound in the illuminated complex; and
   e) correlating the detected transferred energy to a presence or amount of the substantially non-emitting metal in the solution.

2. A method according to claim 1 wherein the substantially non-emitting metal is gadolinium.

3. A method according to claim 1 wherein the first compound is carbostyril124-diethylenetriaminepentaacetic acid (cs124-DTPA).

4. A method according to claim 1 wherein the substantially non-emitting metal exists in a complex with a chelator.

5. A method for detecting presence of a substantially non-emitting metal bound to a chelator in a solution, comprising:
   a) binding a sensitizer to the chelator of the substantially non-emitting metal thereby creating a sensitized-metal complex in the solution;
   b) exposing the complex to a source of illumination to cause the sensitizer to enter into an excited state while the metal in the complex remains substantially non-emitting;
   c) adding an unsensitized chelate to the solution;
   d) detecting a signal from the unsensitized chelate which represents energy transferred from the excited state of the sensitizer; and
   e) correlating the detected signal from the unsensitized chelate to a presence of the substantially non-emitting metal in the solution.

6. A method according to claim 5 wherein the substantially non-emitting metal is gadolinium.

7. A method according to claim 5, further comprising the step of complexing the substantially non-emitting metal with the chelator.

8. A method according to claim 5 wherein the sensitizer is carbostyril124 (cs124).

9. A method according to claim 5 wherein the unsensitized chelate is selected from the group consisting of terbium (Tb) and europium (Eu).

10. A method according to claim 5 wherein the signal being detected is a fluorescent signal.

11. A method according to claim 5 wherein the detecting a signal is performed by electron plasma resonance (EPR).

12. A method according to claim 5 wherein the detecting a signal is performed by nuclear magnetic resonance (NMR).

13. A method according to claim 5 wherein the sensitizer and the unsensitized chelate are conjugated to a phospholipid.

14. A method for detecting amount of or concentration of a substantially non-emitting metal bound to a chelator in a solution comprising:
   a) binding a sensitizer to the chelator of the substantially non-emitting metal thereby creating a sensitized-metal complex in the solution;
   b) exposing the complex to a source of illumination to cause the sensitizer to enter into an excited state while the metal in the complex remains substantially non-emitting;
   c) adding an unsensitized chelate to the solution;
   d) detecting a signal from the unsensitized chelate which represents energy transferred from the excited state of the sensitizer; and
   e) correlating the detected signal from the unsensitized chelate to an amount or concentration of the substantially non-emitting metal in the solution.

15. A method according to claim 14 wherein the substantially non-emitting metal is gadolinium.

16. A method according to claim 14, further comprising the step of complexing the substantially non-emitting metal with the chelator.

17. A method according to claim 14 wherein the sensitizer is carbostyril124 (cs124).

18. A method according to claim 14 wherein the unsensitized chelate is selected from the group consisting of terbium (Tb) and europium (Eu).

19. A method according to claim 14 wherein the signal being detected is a fluorescent signal.

20. A method according to claim 14 wherein the detecting a signal is performed by electron plasma resonance (EPR).

* * * * *